United States Patent
Hicks-Garner et al.

(10) Patent No.: US 9,625,410 B1
(45) Date of Patent: Apr. 18, 2017

(54) SUBSTANCE DETECTION DEVICE AND METHOD

(75) Inventors: Jocelyn Hicks-Garner, Venice, CA (US); Adam F. Gross, Santa Monica, CA (US); Tina T. Salguero, West Hills, CA (US)

(73) Assignee: HRL Laboratories, LLC, Malibu, CA (US)

( * ) Notice: Subject to any disclaimer, the term of this patent is extended or adjusted under 35 U.S.C. 154(b) by 1588 days.

(21) Appl. No.: 12/885,413

(22) Filed: Sep. 17, 2010

(51) Int. Cl.
*G01N 27/327* (2006.01)
*C12Q 1/00* (2006.01)

(52) U.S. Cl.
CPC ........... *G01N 27/327* (2013.01); *C12Q 1/004* (2013.01); *G01N 27/3273* (2013.01)

(58) Field of Classification Search
CPC ... G01N 27/327; G01N 27/3273; C12Q 1/004
See application file for complete search history.

(56) References Cited

U.S. PATENT DOCUMENTS

| | | | |
|---|---|---|---|
| 6,270,649 B1 * | 8/2001 | Zeikus et al. | 205/413 |
| 7,250,288 B2 | 7/2007 | Zeikus et al. | |
| 7,368,190 B2 * | 5/2008 | Heller et al. | 429/2 |
| 2004/0245101 A1 * | 12/2004 | Willner et al. | 204/403.01 |
| 2008/0094624 A1 | 4/2008 | Harsh et al. | |
| 2008/0124585 A1 * | 5/2008 | Schilling | 429/2 |
| 2008/0286624 A1 | 11/2008 | Lovley et al. | |
| 2009/0017512 A1 | 1/2009 | May et al. | |
| 2010/0119920 A1 | 5/2010 | Logan et al. | |
| 2010/0213057 A1 * | 8/2010 | Feldman et al. | 204/403.14 |
| 2010/0221644 A1 * | 9/2010 | Nakagawa et al. | 429/523 |

FOREIGN PATENT DOCUMENTS

| | | |
|---|---|---|
| WO | 2008103028 A1 | 8/2008 |
| WO | 2008/152841 | * 12/2008 |

OTHER PUBLICATIONS

Mia Kim, et al., A novel biomonitoring system using microbial fuel cells, J. Environ. Monit., 2007, 9, 1323-1328, The Royal Society of Chemistry.
Derek R. Lovley, Microbial Energizers: Fuel Cells That Keep on Going, Microbe, 2006, 1(7), 323-329.
Martin Lanthier, et al., Growth with high planktonic biomass in Shewanella oneidensis fuel cells, FEMS Microbiol Lett, 2008, 278, 29-35, Blackwell Publishing Ltd.
Gemma Reguera, et al., Biofilm and Nanowire Production Leads to Increased Current in Geobacter sulfurreducens Fuel Cells, Applied and Environmental Microbiology, 2006, 72(11), 7345-7348, American Society for Microbiology.

* cited by examiner

*Primary Examiner* — Melanie Y Brown
(74) *Attorney, Agent, or Firm* — North Shore Associates

(57) ABSTRACT

Devices and methods are employed to detect substances in a medium. The device comprises an electrogenic bacterium that selectively interacts with a substance to produce electrons. A portion of the electrons provides power to the device and a portion of the electrons generates a signal as an indication of the presence of a substance in the medium. The method comprises contacting the electrogenic bacterium of the device with a medium suspected of containing the substance and measuring the signal generated by the electrons.

20 Claims, 5 Drawing Sheets

SUBSTANCE DETECTION DEVICE AND METHOD

CROSS-REFERENCE TO RELATED APPLICATIONS

N/A

STATEMENT REGARDING FEDERALLY SPONSORED RESEARCH OR DEVELOPMENT

N/A

BACKGROUND

1. Technical Field

The present invention pertains to the detection of substances.

2. Description of Related Art

Detection of substances plays an important role in the health and safety of individuals as well as the community at large. With respect to safety, detection of controlled substances, for example, is especially critical at points of entry into countries, transportation hubs, sensitive facilities (e.g., nuclear and other power plants) and buildings. Securing transportation hubs such as, for example, airports, bus and train stations and cargo and passenger ship terminals from controlled substances such as, for example, explosives, nuclear material, drugs such as drugs of abuse, pathogens and food and their component parts has been complicated by the large volume of luggage and other cargo moved through airports each day.

Various detection systems have been developed for the detection of explosives and controlled substances. Some techniques utilize radiation to inspect cargo such as, for example, both checked and carry-on luggage and other articles. These techniques often involve cumbersome and expensive equipment and visual inspection, which can be time-consuming and hazardous to individuals supervising the inspection. Accordingly, physical inspection, although a widely practiced and important technique, is slow, cumbersome, labor intensive and dependent on the training of the individual conducting the inspection. Current techniques include indirect methods that rely on the presence of vapor emanating from suspect material. One such indirect method, for example, employs dogs trained to sniff preferentially for explosives and narcotics. Techniques other than bulk surveillance are directed at detection of trace amounts of chemical substances adhering to an object such as, for example, clothing and baggage. Trace detection techniques for detecting explosives include, for example, chemiluminescence methods, fluorescence methods, light absorption methods, ion mobility methods, chromatographic methods and mass analysis methods.

Another area of interest is the detection of occupational and environmental substances such as pollutants, contaminants and other substances of interest. Numerous applications require the determination of the presence or absence of one or more substances in a sample. In a particular example, the presence or absence of a substance in a fluid sample may be required such as, for example, liquid or gaseous effluent or emissions from stationary or mobile sources. One important area is the detection of vehicle malfunctions such as, for example, substances leaking from various vehicle parts that include, e.g., engines, drive shafts, exhaust systems and components of electrical systems. Monitoring levels of volatile organic compounds is another important environmental area. Detection of chemical hazards such as carbon monoxide leaks and nature gas leaks is of great interest.

With regard to health, the clinical diagnostic field has seen a broad expansion in recent years, both as to the variety of materials of interest that may be readily and accurately determined, as well as the methods for the determination. Convenient, reliable and non-hazardous means for detecting the presence of low concentrations of materials in liquids is desired. The need to determine many analytes in blood and other biological fluids has become increasingly apparent in many branches of medicine. In endocrinology the knowledge of plasma concentration of a number of different hormones is often required to resolve a diagnostic problem or a panel of markers for a given diagnosis where the ratios could assist in determining disease progression. An even more pressing need is evident in other areas such as allergy testing and the screening of transfused blood for viral contamination or genetic diagnosis.

There remains a need for simple devices and methods for the accurate, sensitive and relatively quick and inexpensive detection of substances. The devices should not have external power supply requirements and should be useable in situ at both proximate and remote locations with remote detection of signal being desirable.

SUMMARY

An embodiment of the present invention is directed to a device for detecting a substance in a medium. The device comprises an electrogenic bacterium that selectively interacts with the substance to produce electrons. A portion of the electrons provides power to the device and a portion of the electrons generates a signal as an indication of the presence of the substance in the medium.

Another embodiment of the present invention is directed to a device for detecting an analyte in a medium. The device comprises (a) a first electrode comprising an electrogenic bacterium wherein the electrogenic bacterium is a genetically modified bacterium that is selectively reactive with a substance to generate electrons and wherein the substance is the analyte or is produced as a result of the presence of the analyte in the medium, (b) a second electrode that is an electron acceptor of electrons produced at the first electrode wherein electrons are received from the first electrode to provide power to the device, and (c) a signal generator that produces a signal from the electrons.

Another embodiment of the present invention is a method of detecting an analyte in a medium. The method comprises contacting the medium with a first electrode of a device as described above, measuring the signal from the signal generator, and relating the amount of signal to one or both of the presence and the amount of the analyte in the medium.

Another embodiment of the present invention is a method of detecting an analyte in a medium. The medium is contacted with an electrogenic bacterium that selectively interacts with the analyte or a substance produced as a result of the presence of the analyte in the medium to produce electrons. A portion of the electrons provides power and a portion of the electrons generates a signal as an indication of the presence of the substance in the medium. The signal is measured.

BRIEF DESCRIPTION OF THE DRAWINGS

The drawings provided herein are for the purpose of facilitating the understanding of certain embodiments of the present invention and are provided by way of illustration and not limitation on the scope of the appended claims. Furthermore, dimensions of elements shown in the drawings may be exaggerated to more clearly show details. As such, the drawings and description are to be regarded as illustrative in nature and not restrictive.

DESCRIPTION OF SPECIFIC EMBODIMENTS

Figure 1:
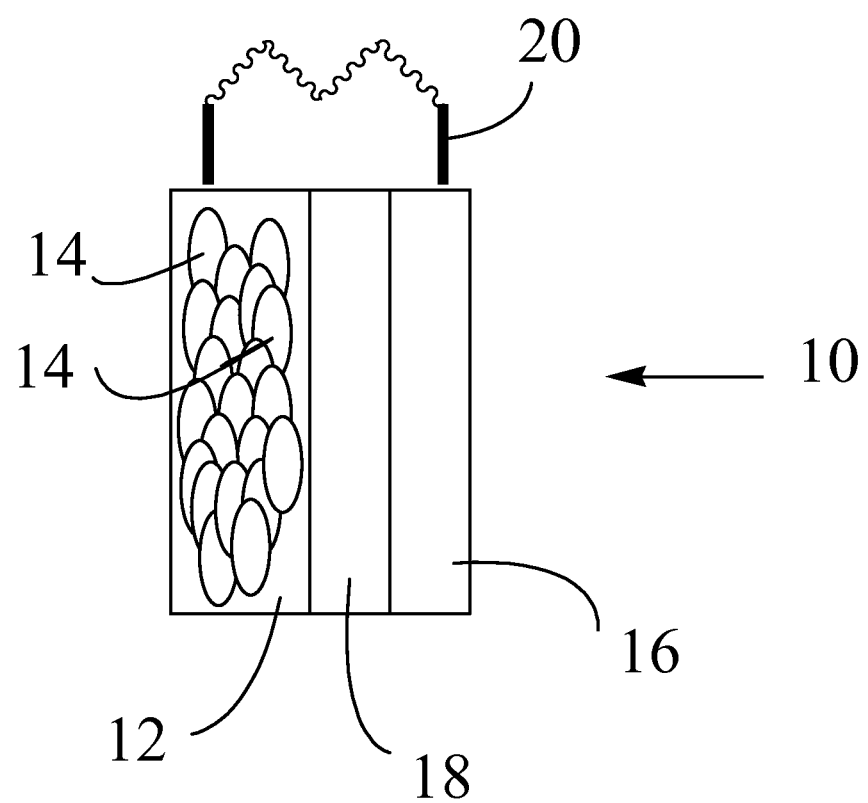
FIG. 1 is a schematic depiction of a device according to an embodiment of the present invention.

Embodiments of the present invention are directed to detection devices that are self-powered and respond selectively to a substance of interest. Embodiments of the present devices generate a signal, without interrogation, that can be detected remotely. In addition, embodiments of the present devices are configurable for many different substances and for different areas and locations of use. Some embodiments of the present devices may be employed in locations where other sensing systems cannot be placed because such systems require, for example, an external power source or complex circuitry. Some embodiments of the present devices are highly sensitive (part per million or parts per billion range, for example) and selective based on the specificity of an electrogenic bacterium for a substance of interest. The shelf-life potential of some embodiments of the present devices is substantial since the electrogenic bacterium can remain in a dormant state until a medium containing an analyte is brought into contact with the bacterium thereby placing a device in an "on state" from an "off state."

Some embodiments of the present invention are directed to devices for detecting a substance in a medium. The device comprises an electrogenic bacterium that selectively interacts with the substance to produce electrons. A portion of the electrons provides power to the device by assisting in the completion of the metabolic cycle of the electrogenic bacterium and a portion of the electrons generates a signal as an indication of the presence of the substance in the medium.

The electrogenic bacterium is any bacterium that acts upon a substrate and generates electrons as part of its metabolic cycle. In the presence of a substrate, the electrogenic bacterium has the ability to metabolize the substrate, which is oxidized with the release of one or more of protons, electrons and chemical by-products. In the present embodiments the electrogenic bacterium acts upon the substance of interest as a substrate and electrons are produced that may be employed as a power source for a device as well as being a detectable entity. The electrogenic bacterium may be naturally occurring or genetically modified, gram-negative or gram-positive, anaerobic or aerobic, mesophilic or thermophilic. Examples of electrogenic bacterium, by way of illustration and not limitation, include bacteria from the following families: *Geobacter, Shewanella, Desulfovibrio, Desulfuromonas, Desulfuromusa, Desulfobulbus, Enterobacter, Pelobacter, Malonomonas, Thermincola*, and *Deferribacteres*.

Specific examples of electrogenic bacteria, by way of illustration and not limitation, include *Geobacter sulfurreducens, Geobacter metallireducens, Geobacter argillaceus, Geobacter bemidjiensis, Geobacter bremensis, Geobacter chapellei, Geobacter grbiciae, Geobacter hydrogenophilus, Geobacter pelophilus, Geobacter pickeringii, Geobacter psychrophilus, Geobacter fermentans, Geothrix fermentans, Shewanella putrefaciens, Shewanella abyssi, Shewanella affinis, Shewanella algae, Shewanella algidipiscicola, Shewanella amazonensis, Shewanella acquimarina, Shewanella atlantica, Shewanella baltica, Shewanella basaltis, Shewanella benthica, Shewanella canadensis, Shewanella chilikensis, Shewanella colwelliana, Shewanella decolorationis, Shewanella dentrificans, Shewanella don ghaensis, Shewanella fidelis, Shewanella frigidimarina, Shewanella gaetbuli, Shewanella gelidimarina, Shewanella glacialipiscicola, Shewanella halfniensis, Shewanella halifaxensis, Shewanella haliotis, Shewanella hanedai, Shewanella irciniae, Shewanella japonica, Shewanella kaireitica, Shewanella livingstonensis, Shewanella loihica, Shewanella marina, Shewanella marinintestina, Shewanella marisfiavi, Shewanella morhuae, Shewanella olleyana, Shewanella oneidensis, Shewanella pacifica, Shewanella paeleana, Shewanella piezotolerans, Shewanella pneumatophori, Shewanella profunda, Shewanella psychrophila, Shewanella sairae, Shewanella schlegeliana, Shewanella sediminus, Shewanella spongiae, Shewanella surugensis, Shewanella vesiculosa, Shewanella violacea, Shewanella waksmanii, Shewanella woodyi, Enterobacter aerogenes, Enterobacter cloacae, Enterobacter agglomerans, Enterobacter amnigenus, Enterobacter asburia, Enterobacter cancerogenus, Enterobacter cloacae* subsp. *cloacae, Enterobacter cloacae* subsp. *dissolvens, Enterobacter cowanii, Enterobacter dissolvens, Enterobacter gergoviae, Enterobacter helveticus, Enterobacter hormaechei, Enterobacter intermedius, Enterobacter kobei, Enterobacter ludwigii, Enterobacter nimipressuralis, Enterobacter oryzae, Enterobacter pulveris, Enterobacter pyrinus, Enterobacter radicincitans, Enterobacter sakazakii, Enterobacter taylorae, Enterobacter turicensis, Desulfovibrio spp, Desulfovibrio desulfuricans, Desulfovibrio acrylicus, Desulfovibrio aerotolerans, Desulfovibrio aespoeensis, Desulfovibrio africanus, Desulfovibrio alaskensis, Desulfovibrio alcoholivorans, Desulfovibrio alkalitolerans, Desulfovibrio aminophilus, Desulfovibrio baarsii, Desulfovibrio baculatus, Desulfovibrio bastinii, Desulfovibrio bizertensis, Desulfovibrio burkinensis, Desulfovibrio butyratiphilus, Desulfovibrio carbinolicus, Desulfovibrio carbinoliphilus, Desulfovibrio cuneatus, Desulfovibrio dechloracetivorans, Desulfovibrio desulfuricans, Desulfovibrio desulfuricans* subsp. *aestuarii, Desulfovibrio desulfuricans* subsp. *desulfuricans, Desulfovibrio ferrireducens, Desulfovibrio frigidus, Desulfovibrio fructosivorans, Desulfovibrio furfuralis, Desulfovibrio gabonensis, Desulfovibrio giganteus, Desulfovibrio gigas, Desulfovibrio gracilis, Desulfovibrio halophilus, Desulfovibrio hydrothermalis, Desulfovibrio idahonensis, Desulfovibrio indonesiensis, Desulfovibrio inopinatus, Desulfovibrio intestinalis, Desulfovibrio litoralis, Desulfovibrio longreachensis, Desulfovibrio longus, Desulfovibrio magneticus, Desulfovibrio marinus, Desulfovibrio marinisediminis, Desulfovibrio marrakechensis, Desulfovibrio mexicanus, Desulfovibrio oxamicus, Desulfovibrio oxyclinae, Desulfovibrio paquesii, Desulfovibrio piger, Desulfovibrio profundus, Desulfovibrio psychrotolerans, Desulfovibrio putealis, Desulfovibrio salexigens, Desulfovibrio sapovorans, Desulfovibrio senezii, Desulfovibrio simplex, Desulfovibrio sulfodis-* mutans, *Desulfovibrio term itidis, Desulfovibrio thermophilus, Desulfovibrio tunisiensis, Desulfovibrio vietnamensis, Desulfovibrio vulgaris, Desulfovibrio vulgaris* subsp. *oxamicus, Desulfovibrio vulgaris* subsp. *vulgaris, Desulfovibrio zosterae, Desulfobulbus propionicus, Pelobacter carbinolicus, Pelobacter acetylenicus, Pelobacter acidigallici, Pelobacter massiliensis, Pelobacter propionicus, Pelobacter seleniigenes, Pelobacter venetianus, Desulfuromonas acetexigens, Desulfuromonas acetoxidans, Desulfuromonas chloroethenica, Desulfuromonas michiganensis, Desulfuromonas palmitatis, Desulfuromonas svalbardensis, Desulfuromonas thiophila, Desulfuromusa bakii, Desulfuromusa ferrireducens, Desulfuromusa kysingii, Desulfuromusa succinoxidans, Malonomonas rubra, Thermincola carboxydophila, Thermincola ferriacetica* and *Rhodoferax ferrireducens*, for example.

As mentioned above, the electrogenic bacterium acts upon the substance of interest, to the exclusion of other substances, and in the process of doing so electrons are produced. An increase in the number of electrons produced can be equated to one or both of the presence and amount of the substance of interest. The electrogenic bacterium has specificity for the substance of interest. The ability of the electrogenic bacterium to act specifically on the substance of interest may be a natural state of the electrogenic bacterium or may be the result of a genetic modification such as, for example, adaptive evolution to the substance of interest. Any approach to modification of the electrogenic bacterium may be employed as long as the resulting electrogenic bacterium has specificity for the substance of interest.

As indicated above, genetic modification of the electrogenic bacterium may be employed to obtain a bacterium that is selective for a particular substance to the exclusion of other substances. In this manner, the electrogenic bacterium can be genetically modified to respond selectively to a substance of interest, i.e., made to respond preferentially to a substance of interest and ignore similar compounds that are not of interest. For this purpose, "similar compounds" are those compounds with structures or chemical compositions that are related to the substance of interest.

The genetic modification may involve the direct or indirect manipulation of the organism's genes including genetic engineering, environmental engineering and chemical modification, for example. Direct methods of genetic modification include but are not limited to recombinant DNA technology, genetic manipulation, gene splicing, molecular cloning and transformation, cloning, transgenesis, rational design based on computer modeling (in silico methods), gene mapping, gene coding, rational design based on X-ray crystallography data of proteins, and site-directed mutagenesis. Indirect methods of genetic modification include, but are not limited to, traditional selective breeding, natural selection, directed evolution, adaptive evolution, directed mutation, and random mutation. Other approaches to genetic modification of the electrogenic bacterium include, for example, first sequencing the genome of the bacterium of interest, modifying the sequence and then propagating the modified bacterium strain.

In some embodiments a type of genetic modification known as directed or adaptive evolution may be employed. This method involves an algorithm of mutation and natural selection, which may be used to produce modified electrogenic bacteria strains that have optimized performance with respect to analyte selectivity. In their natural environment, electrogenic bacteria adapt to changes in their food supply as a means of survival. Evolutionary pressure may be employed to force the electrogenic bacterium to adapt to an alternate food source (i.e., the substance of interest or analyte), thereby altering its metabolic pathway to respond to the presence of the analyte.

Thus, one method of generating a bacterium that will respond preferentially to a substance is through performing repeated cycles of exposure and propagation. In this method the bacterium is exposed to the substance of interest and then removed from the environment and propagated in a medium containing the substance of interest. This effectively forces bacterium to grow on the substance of interest to survive. By serially performing this process, the bacterium strain most adept at adapting to the change is selected and propagated.

An example of a stepwise process for selection of a bacterium is presented below by way of illustration and not limitation. In a first step, the analyte and a compatible electrogenic bacterium are identified. The electrogenic bacterium should be selected based on its ability to metabolize the analyte. In a next step, the electrogenic bacterium is subjected to genetic modification by, for example, directed evolution to develop metabolic sensitivity to the analyte. The process requires multiple iterations of the chosen adaptive evolution process, such as, e.g., serial exposure to select for the desired mutations. The effectiveness of this process is determined by the propagation of the bacterium when exposed to the analyte. After it has been determined that the bacterium is capable of metabolizing the analyte, electricity production during this process of metabolization should be confirmed. Electricity production can be examined by using the evolved bacterium in a microbial fuel cell employing the analyte as the fuel source. If additional selectivity is required, methods to further detection of the analyte can be implemented. For example, oxidation potential can be monitored to distinguish similar molecules or selectively permeable membranes or functionalized electrodes may be employed.

In some embodiments the electrogenic bacterium is associated with a solid support. The term "associated with" means that the electrogenic bacterium may be on the surface of the solid support or may be incorporated into a solid support or a combination of both. The manner in which the electrogenic bacterium is associated with the support depends on one or more of the nature of the electrogenic bacterium, the nature of the substance on which the electrogenic bacterium acts, the nature of the support, and the application for which the system is designed, for example. The electrogenic bacterium should be associated with the support so that a significant portion of the electrogenic bacterium is available for exposure to and reaction with the substance of interest.

In some embodiments the support has a surface area of about 10 $cm^2/cm^3$ to about 100 $cm^2/cm^3$, or about 10 $cm^2/cm^3$ to about 90 $cm^2/cm^3$, or about 10 $cm^2/cm^3$ to about 80 $cm^2/cm^3$, or about 10 $cm^2/cm^3$ to about 70 $cm^2/cm^3$, or about 10 $cm^2/cm^3$ to about 60 $cm^2/cm^3$, or about 10 $cm^2/cm^3$ to about 50 $cm^2/cm^3$, or about 10 $cm^2/cm^3$ to about 40 $cm^2/cm^3$, or about 10 $cm^2/cm^3$ to about 30 $cm^2/cm^3$, or about 10 $cm^2/cm^3$ to about 20 $cm^2/cm^3$, or about 20 $cm^2/cm^3$ to about 100 $cm^2/cm^3$, or about 20 $cm^2/cm^3$ to about 90 $cm^2/cm^3$, or about 20 $cm^2/cm^3$ to about 80 $cm^2/cm^3$, or about 20 $cm^2/cm^3$ to about 70 $cm^2/cm^3$, or about 20 $cm^2/cm^3$ to about 60 $cm^2/cm^3$, or about 20 $cm^2/cm^3$ to about 50 $cm^2/cm^3$, or about 20 $cm^2/cm^3$ to about 40 $cm^2/cm^3$, or about 20 $cm^2/cm^3$ to about 30 $cm^2/cm^3$, or about 30 $cm^2/cm^3$ to about 100 $cm^2/cm^3$, or about 30 $cm^2/cm^3$ to about 90 $cm^2/cm^3$, or about 30 $cm^2/cm^3$ to about 80 $cm^2/cm^3$, or about 30 $cm^2/cm^3$ to about 70 $cm^2/cm^3$, or about 30 $cm^2/cm^3$ to about 60 $cm^2/cm^3$, or about 30 $cm^2/cm^3$ to about 50 cm²/cm³, or about 30 cm²/cm³ to about 40 cm²/cm³, or about 10 cm²/cm³ to about 30 cm²/cm³, or about 10 cm²/cm³ to about 20 cm²/cm³, for example, with at least 80%, or at least 85%, or at least 90%, or at least 95%, or at least 99% of the support surface having the electrogenic bacterium.

The amount of the electrogenic bacterium associated with the support is dependent on one or more of the nature of the electrogenic bacterium including size and packing density, the size and nature of the support, the nature and amount of the substance of interest, the power requirements of a device comprising the electrogenic bacterium, for example. In some embodiments the electrogenic bacterium is a film (such as, e.g., a biofilm) on the surface of a support and the thickness of the film is about 5 to about 150 microns, or about 5 to about 125 microns, or about 5 to about 100 microns, or about 5 to about 80 microns, or about 5 to about 70 microns, or about 5 to about 60 microns, or about 5 to about 50 microns, or about 5 to about 40 microns, or about 5 to about 30 microns, or about 5 to about 20 microns, or about 5 to about 10 microns, or about 10 to about 150 microns, or about 10 to about 125 microns, or about 10 to about 100 microns, or about 10 to about 90 microns, or about 10 to about 80 microns, or about 10 to about 70 microns, or about 10 to about 60 microns, or about 10 to about 50 microns, or about 10 to about 40 microns, or about 10 to about 30 microns, or about 10 to about 20 microns, or about 20 to about 100 microns, or about 20 to about 90 microns, or about 20 to about 80 microns, or about 20 to about 70 microns, or about 20 to about 60 microns, or about 20 to about 50 microns, or about 20 to about 40 microns, or about 20 to about 30 microns, or about 30 to about 100 microns, or about 30 to about 90 microns, or about 30 to about 80 microns, or about 30 to about 70 microns, or about 30 to about 60 microns, or about 30 to about 50 microns, or about 30 to about 40 microns, for example. In some embodiments, the thickness of the film may be determined empirically.

In some embodiments the electrogenic bacterium is a coating on the surface of a support. As mentioned above, in some embodiments the electrogenic bacterium is a film on the surface of a support. The manner in which the electrogenic bacterium is deposited as a coating or a film on the surface of a support depends on one or more of the nature of the electrogenic bacterium, the nature of the substance on which the electrogenic bacterium acts, the nature of the support and any coatings applied to the support to promote adhesion, for example. In an embodiment, the electrogenic bacterium may be a biofilm on the surface of the support produced, for example, by one or more of the following processes: growing the bacterium on one or more of the surface and interior of the support by spraying a film of bacterium on the surface of the support, by transferring bacteria from one surface to another by placing to surfaces in contact. In some embodiments the electrogenic bacterium is associated with the support by inoculating the support with a substantially pure population of the electrogenic bacterium and allowing propagation of the electrogenic bacterium. Conditions for such propagation include, for example, providing nutrients such as, e.g., minerals and vitamins that promote the health and viability of the bacteria. The propagation is continued until the desired density of electrogenic bacterium is associated with the support.

The support may be fabricated from any material suitable as a foundation for the electrogenic bacterium. The support should be non-toxic to the electrogenic bacterium. The support may be comprised of an inorganic or organic, solid, semi-solid (including gels) or fluid, water insoluble material, which may be porous or non-porous. Such materials include, for example, glass, metals, alloys, carbon, graphite, ceramics, semiconductor materials and plastics, and a combination of two or more of the above materials. The material for the support may be transparent, translucent or opaque depending on, for example, the manner in which the device is to be used. The support can have any of a number of shapes, such as a strip, a rod, a particle including bead, a film, a membrane, a tube, a well, planar surfaces such as, e.g., plate and sheet, a fiber or a foam, for example. The surface of the support may be rough or smooth, have rough or smooth portions or a combination of smooth and rough portions. The size and shape of the support depends on one or more of the size and nature of a device in which the support is contained and the manner in which the device is to be used, for example.

In some embodiments the support is an electrode that is electrically conductive, durable, structurally robust and non-toxic to the electrogenic bacterium. The electrode may be formed from materials such as, but not limited to, carbon, graphite, conductive metals such as, for example, gold, platinum, palladium, cobalt, selenium, vanadium and tungsten, and combinations, alloys, oxides, sulfides and halides thereof, and including metal oxides such as, but not limited to, tin oxide, zinc oxide, indium oxide, indium tin oxide, ruthenium oxide and indium zinc oxide; conductive polymers such as, for example, polyaniline, polypyrrole, polythiophene, and polyphenylene sulfide and metalized polymers. Each of the aforementioned materials may be used individually or in combination and the electrode may be formed in a single layer construction or a multilayer construction. In some embodiments the electrode material comprising the electrogenic bacterium may be, for example, carbon cloth, carbon felt, carbon paper, carbon foam, carbon aerogel, carbon fibers such as, e.g., carbon wool, graphite, porous graphite, packed graphite powder, graphite rods, graphite granules, graphite felt and graphite foam. Each of the aforementioned electrode materials may be used individually or in combination and, as mentioned above, the electrode may be formed in a single layer construction or a multilayer construction.

The substance of interest on which the electrogenic bacterium acts to produce electrons may be an analyte or a substance produced as a result of the presence of an analyte. The substance may be a solid, semi-solid, liquid or a gas and may be present in a fluid medium as, for example, a solution, dispersion, a suspension or an emulsified material. Analytes or substances of interests produced as a result of the presence of an analyte include, by way of illustration and not limitation, volatile organic compounds, semi-volatile organic compounds, proteins, polysaccharides, medications, drugs of abuse, pollutants, toxins, forensic substances, explosive residues, and acid vapors, for example. In some embodiments the analyte may be reactive directly with an electrogenic bacterium. On the other hand, in some embodiments the analyte produces a substance that is reactive with the electrogenic bacterium.

In some embodiments analytes may be present in or on biological fluids such as, for example, blood, plasma and other bodily secretions or extractants; air and other gaseous substances; surfaces of inanimate or animate objects, for example, body appendages, weapons, luggage and other cargo, industrial surfaces, residential surfaces; soil; water; vehicular components; and industrial and residential exhaust systems, for example.

As mentioned above, the substance that reacts with the electrogenic bacterium may be produced as the result of the presence of an analyte in a medium. In one embodiment a specific binding partner for the analyte may be included in the reaction medium. The specific binding partner may be modified in such a way that binding of the analyte to the specific binding partner releases a substance that reacts with the electrogenic bacterium. For example, the specific binding partner may be bound to a substance precursor by a cleavable moiety that is cleaved upon the binding of the analyte to the specific binding partner thereby releasing the substance for reaction with the electrogenic bacterium. In other embodiments the substance may be formed as a result of the presence of the analyte by the analyte cleaving bonds in the substance to make it easier for the bacteria to consume it; the analyte being oxidized by a material in the reaction medium; or the analyte being chemically modified (pre-digested) by enzymes or yeast in the reaction medium, for example. In the embodiments above, the electrogenic bacterium need only have specificity for the substance that is released or formed as a result of the presence of the analyte. Accordingly, in some embodiments the same electrogenic bacterium may be used in different assay devices to assay for many diverse analytes and in that sense the electrogenic bacterium is generic to many different analytes in such embodiments.

In some embodiments the substance is present in a medium, which may be a natural medium or an artificial medium. A natural medium is a source medium of the analyte without extraction of the analyte. The natural medium may be a solid, a liquid or a gas or a combination of two or more of the above. The natural medium may be treated to adjust pH, ionic strength and oxidative potential, for example, and to release the analyte from materials to which the analyte may be bound. The natural medium may be, by way of illustration and not limitation, air; environmental solids, liquids or gaseous wastes; surfaces including walls in a manufacturing facility, for example; and biological solids, semi-solids and fluids such as, for example, body fluids including blood, plasma, secretions or extracted material (extractants) from ears, eyes, throat, nose and other body cavities.

An artificial medium is a medium containing the analyte that has been extracted from a natural medium. The artificial medium may be a liquid or a gas. The medium should be compatible with the electrogenic bacterium and other components of a device comprising the electrogenic bacterium. In some embodiments the analyte is present in the artificial medium as a solution or dispersion. In some embodiments the medium is an aqueous medium, which may be solely water or may include from 0.1 to about 40 volume percent, or from 0.1 to about 35 volume percent, or from 0.1 to about 30 volume percent, or from 0.1 to about 25 volume percent, or from 0.1 to about 20 volume percent of a cosolvent such as, for example, an organic solvent, which may be an alcohol, ether, ester, and the like.

The conditions for the exposure of the artificial or natural medium to the electrogenic bacterium include conditions such as, for example, temperature, pH, duration of exposure and concentration of the analyte in the medium. The conditions are dependent on one or more of the nature of the analyte, the nature of the electrogenic bacterium, the specificity of the bacterium to the analyte, and the amount or existence of similar analytes in the medium, for example. In some embodiments, the temperature for one or both of the use of the device or the storage of the device may be about 0 to about 100° C., or about 10 to about 90° C., or about 15 to about 80° C., or about 15 to about 70° C., or about 15 to about 60° C., or about 20 to about 40° C., for example. In some embodiments the duration of exposure of the electrogenic bacterium to the medium suspected of containing an analyte may be about 10 seconds to many weeks, or about 10 seconds to 1 week, or about 10 seconds to about 24 hours, or about 10 seconds to about 12 hours, or about 10 seconds to about 5 hours, or about 10 seconds to about 2 hours, or about 10 seconds to about 60 seconds, for example. It should be noted that, if the analyte is always in the medium, the bacterium may be exposed to the medium for as long as the bacterium remains alive, which in some embodiments may be essentially indefinitely because of the likelihood that the bacterium can propagate.

In some embodiments the device for detecting an analyte in a medium comprises a first electrode, a second electrode and a signal generator. The first electrode comprises an electrogenic bacterium that is reactive with a substance to generate electrons wherein the substance is the analyte or is produced as a result of the presence of the analyte in the medium. In some embodiments the first electrode is as discussed in more detail above as the electrode support for the electrogenic bacterium. The dimensions of the first electrode are dependent on, for example, one or more of the nature of the device, the nature of the analyte and the medium containing the analyte, the duration of use, the nature and amount of the electrogenic bacterium and the required sensitivity of the device, for example. The dimensions of the first electrode are dependent the size of the device, the manner in which the device will be used and the placement of the device, for example. In some embodiments the size of the first electrode will be on the micron level and in some embodiments the size of the first electrode will be on the meter level, or anywhere in between. As mentioned above, a portion of the generated electrons is used by the electrogenic bacterium to complete its respiratory cycle, thus rendering the device self-powered.

The second electrode is an acceptor of electrons produced at the first electrode. The second electrode is electrically conducting and should not be fouled easily if exposed to air or other ambient conditions. The second electrode may be a metal such as, for example, gold or platinum, or a combination of two or metals; an organic compound such as, for example, a conductive polymer; a gas such as, for example, oxygen; carbon materials such as, e.g., carbon cloth, carbon felt, carbon paper, carbon foam, carbon aerogel, carbon fibers such as, e.g., carbon wool; and graphite materials such as, e.g., porous graphite, packed graphite powder, graphite rods, graphite granules, graphite felt and graphite foam. Each of the aforementioned electrode materials may be used individually or in combination and, as mentioned above, the electrode may be formed in a single layer construction or a multilayer construction.

As mentioned above, in some embodiments a portion of the electrons produced by the action of the electrogenic bacterium on the substance is transferred through electronics or electrical circuitry from the first electrode to the second electrode. In this way the transferred electrons may be used to perform work. In some embodiments the electronics comprise one or more of resistors, capacitors, inductors, semiconductor devices, integrated circuits, transistor-transistor logic devices, antennas, light emitting diodes and quartz crystal oscillators.

In some embodiments the work performed is the generation of a signal that may be detected and quantitated to determine one or more of the presence and amount of the analyte in the medium. In some embodiments the signal generator generates a signal without interrogation and the signal can be detected remotely. The phrase "without interrogation" means that the signal is generated without being queried, that is, a signal is periodically sent by the system based on time or when a certain level of the analyte is detected. In some embodiments detector electronics are employed as part or all of a signal generator. The nature of the detector electronics depends on the nature of the signal, for example. The signal generated may be an RF signal, a colorimetric signal or a chemical signal, for example. For an RF signal, the electronics may include, for example, an antenna and a quartz crystal oscillator. For a colorimetric signal, the electronics may include, for example, an electrochromic device, a battery and a diode. For a chemical signal, the electronics may include, for example, a resistive heater or an electrochemical half cell.

In some embodiments the detector electronics can include a capacitor for storing a portion of the electrons produced as a result of the presence of an analyte and the capacitor can be examined subsequently to relate the amount of stored electrons to one or both of the presence and amount of analyte present in a medium. In this embodiment, the current from the detector does not need to produce a signal immediately. The current may be used to charge a capacitor or battery, which will be used to power a signal at a later time or to be interrogated remotely.

Embodiments of the present devices can also use differences in oxidation potential to distinguish chemically similar compounds. If the analyte is very similar in molecular weight and composition to another compound in the environment, the present devices can distinguish the analyte from such similar compound by registering the difference in the oxidation or reduction potentials of the two materials. For example, the ability to distinguish between an aromatic ring structure containing one, two or three nitrogen groups on this basis may be carried out. For example, the addition of a functional group (e.g., nitro group) to an aromatic ring will cause the compound's oxidation potential to shift by 0.15V or more. Such a difference in oxidation potential can be readily detected by embodiments of the present device. In this way, embodiments of the present devices provide two means of detection selectivity: the primary means is the metabolism of genetically sensitive electrogenic bacteria and the secondary means is the use of distinguishing oxidation potentials.

In some embodiments the device comprises a separator between the first electrode and the second electrode. The separator is a porous membrane placed between the electrodes of opposite polarity. The primary function of the separator is to avoid electrical contact between the electrodes, thereby preventing electrical short circuits, while permitting flow through the membrane of some products of the reaction of a substance with the electrogenic bacterium. Such reaction produces, for example, carbon dioxide, protons and electrons. The electrons are transferred to the first electrode and then, through an electronic circuit, to the second electrode. Protons pass through the separator to the second electrode where they can react with materials such as, for example, oxygen to form water. The separator is an electronic insulator and has the ability to conduct ions such as, e.g., cations. To the extent necessary, the separator should assist in avoiding any processes that would adversely affect the operation of the device. The pore size is dependent on the particular application for the device and the separator. In some embodiments the separator comprises pores of average diameter size of 1 to about 50 microns, or 1 to about 40 microns, or 1 to about 30 microns, or 1 to about 20 microns, or 1 to about 10 microns, or about 5 to about 45 microns, or about 5 to about 35 microns, or about 5 to about 25 microns, or about 5 to about 15 microns, or about 10 to about 45 microns, or abut 10 to about 35 microns, or about 10 to about 25 microns, or about 20 to about 50 microns, or about 20 to about 40 microns, or about 20 to about 30 microns, or about 25 microns.

Typical commercial membranes that may be employed as a proton conducting membrane include, by way of example and not limitation, sulfonated tetrafluoroethylene based fluoropolymer-copolymer membranes such as, e.g., NAFION™ N117 membrane (from E. I. du Pont de Nemours and Company, Wilmington Del.); perfluorinated sulfonic acid polymer membranes such as, e.g., ACIPLEX™ membranes (from Asahi Glass Co., Japan); polymer membranes made by Dow Chemical Co. such as XUS13204.10; membranes of polyethylene and polypropylene sulfuric acid, polystyrene sulfuric acid and other polyhydrocarbon-based sulfuric acids (such as membranes made by RAI Corporation, USA); polyfluoro-polyaryl sulfonic acid membranes; perfluoropolyaryl sulfonic acid membranes; and composite membranes consisting of two or more types of proton conducting cation-exchange polymers with various acid equivalent weight and chemical composition; for example.

The thickness of the separator depends on one or more of the nature of the electrogenic bacterium, the nature of the electrode material, the nature of the medium suspected of containing the analyte, the nature of the analyte and the nature of the reaction medium, for example. The thickness of the separator is that which is sufficient to accomplish the primary function of the separator, namely, to avoid electrical contact between the electrodes.

In some embodiments the device as described above may be confined in a housing that provides an environmental barrier. The nature of the housing such as, for example, the size of the housing and the manner and materials for construction of the housing, is dependent on one or more of the nature of the electrodes, the nature of the electrogenic bacterium, the nature of the signal generator, the nature of the signal produced, the nature of the electronic circuits, and the nature of the environment in which the device is to be employed, for example. The housing may be manufactured from any suitable material that provides for the appropriate environmental barrier. Such materials include, by way of illustration and not limitation, plastics, glass, permeable polymers and porous metals, for example.

Some embodiments of the present invention are directed to an apparatus to analyze for one or more of the presence and amount of an analyte or a substance produced as the result of the presence of the analyte. The apparatus comprises one, two, three, four or more devices as described above in a housing. Each device within the apparatus may be designed for analyzing for the same analyte or for different analytes depending on the nature of the environment in which the apparatus is to be employed, for example. In some embodiments each device that comprises the apparatus may be in a separate housing within the apparatus, which further comprises a housing to contain the housed devices. In some embodiments the devices may all be housed within a single housing.

The construction of the device and the apparatus allows the devices and apparatus to be configured for a particular environment and use. This configurable nature of the device allows the apparatus and devices to be used in locations where other sensing systems cannot be placed due to, for example, the need for an external power source and complex circuitry. The size of embodiments of the present device and the lack of need for battery power, for example, contribute to the ease of use of the devices and apparatus of the present embodiments. In some embodiments the device is capable of unattended operation. Furthermore, the devices can continue to function after detecting an analyte.

The devices can be placed in multiple environmental locations in and around commercial and residential buildings, in industrial plants and industrial areas and in transportation centers, for example. The devices in accordance with embodiments of the present invention can remain in an "off" state until the device comes into contact with a medium containing an analyte. In some embodiments the present devices are not single use devices. For example, every time the device comes into contact with a medium containing an analyte, electrons will be generated to produce a signal. Thus, some embodiments of the present devices, apparatus and methods allow determination of the frequency of contact with a target.

An embodiment of a detection device as discussed above is depicted in FIG. 1.

Referring to FIG. 1, detection device 10 comprises electrode 12, which has electrogenic bacterium 14 coated on its surface. Electrode 16 is separated from electrode 12 by separator 18. Electronic circuit 20 electrically connects electrode 12 and electrode 16.

As mentioned above, an embodiment of the present invention is a method of detecting an analyte in a medium. The medium is contacted with an electrogenic bacterium that selectively interacts with the analyte or a substance produced as a result of the presence of the analyte in the medium to produce electrons. A portion of the electrons provides power to the device and a portion of the electrons generates a signal as an indication of the presence of the substance in the medium. The signal is measured.

Figure 2:
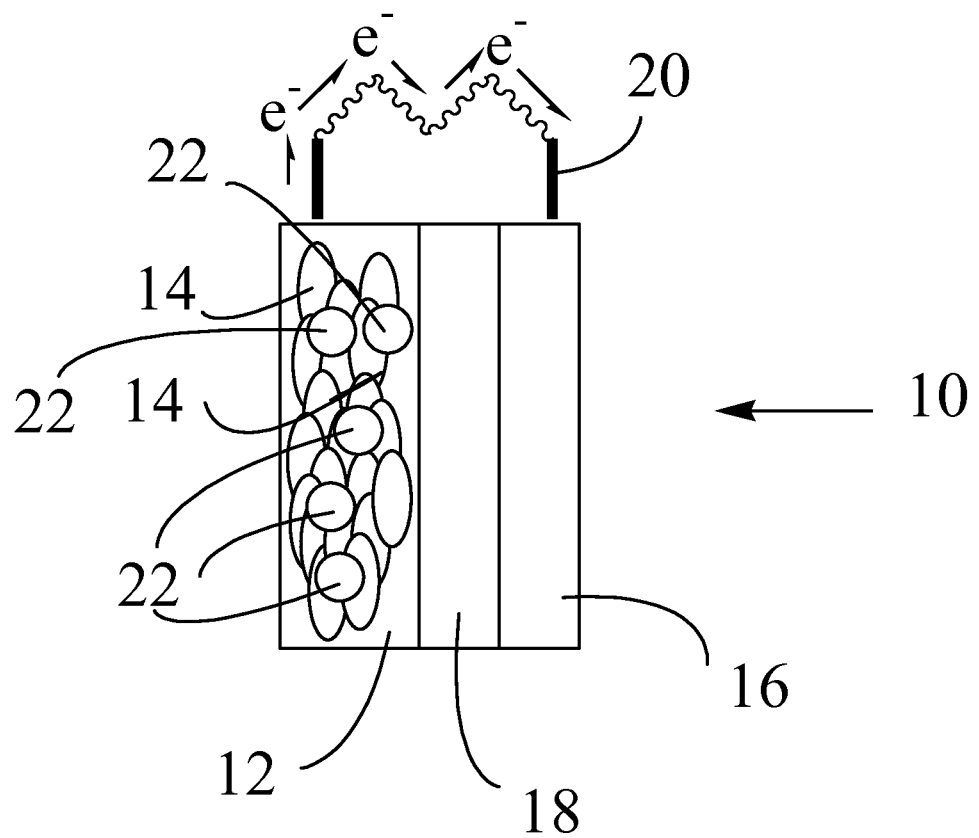
FIG. 2 is a schematic depiction of a device exposed to a medium containing an analyte according to an embodiment of the present invention.

FIG. 2 depicts an example of a method of detecting an analyte 22 in accordance with an embodiment of the present invention. In particular, FIG. 2 illustrates an example of a method of detecting an analyte using detection device 10. Analyte 22 reacts with electrogenic bacterium 14 and electrons e− are produced. A portion of electrons e− is used as a source of energy for the electrogenic bacterium and a portion of electrons e− are transferred through electronic circuit 20 to electrode 16. Electronic circuit 20 comprises, for example, an antenna and a quartz crystal oscillator, to generate an RF signal that is capable of remote detection.

Figure 5:
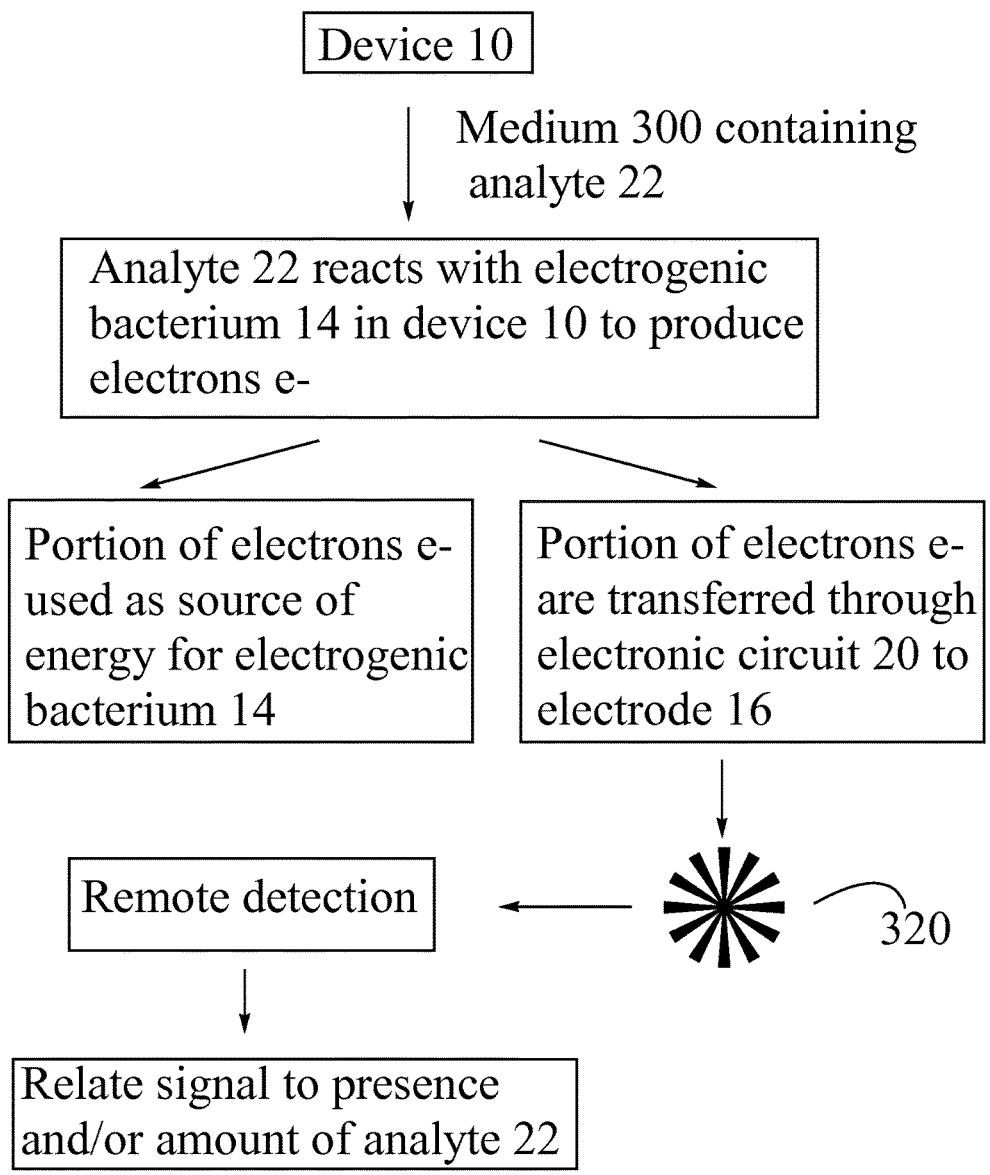
FIG. 5 is a flow chart depicting a method for detecting an analyte using a device according to an embodiment of the present invention.

The flow chart in FIG. 5 further depicts an embodiment of a method as described above. Referring to FIG. 5, detection device 10 is exposed to medium 300 containing analyte 22. Electrogenic bacterium 14 of detection device 10 reacts with analyte 22 to generate electrons e−. A portion of electrons e− are used as a source of energy for electrogenic bacterium 14 and a portion of electrons e− are transferred through electronic circuit 20 to electrode 16 and RF signal 320 is generated. Signal 320 is detected from a remote location and the amount of signal 320 is related to one of both of the presence and amount of analyte 22 in medium 300.

Figure 3:
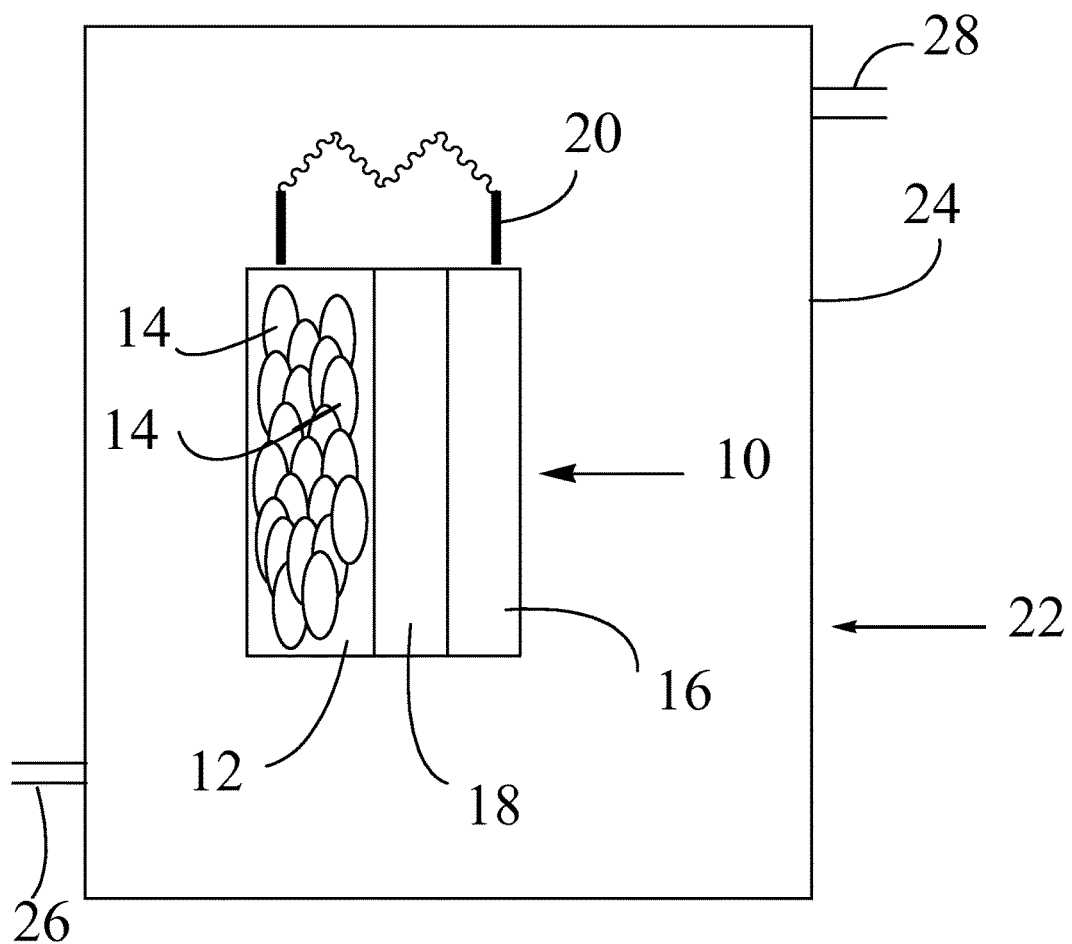
FIG. 3 is a schematic depiction of an apparatus comprising a device according to an embodiment of the present invention.

An embodiment of an apparatus comprising detection device 10 is depicted in FIG. 3. Apparatus 22 comprises housing 24 within which detection device 10 is contained. Housing 24 comprises inlet 26 and outlet 28 for admitting a medium suspected of containing an analyte into housing 24.

Figure 4:
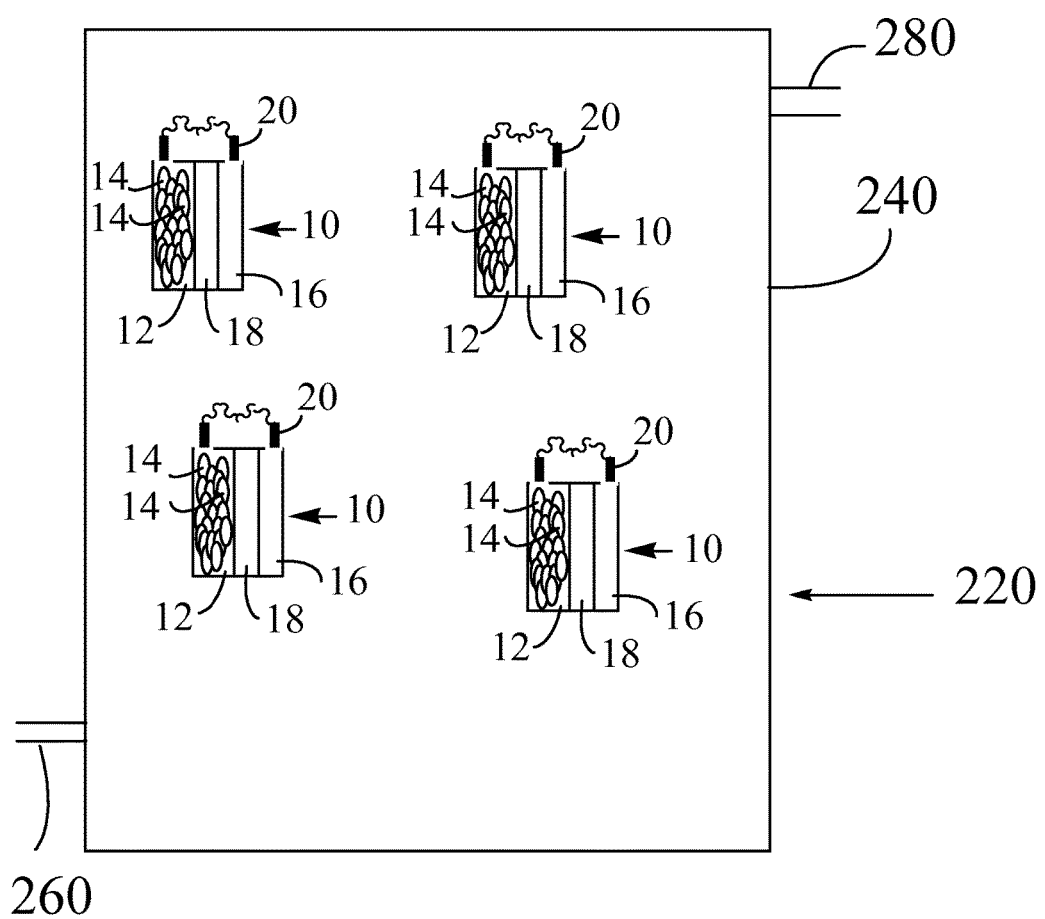
FIG. 4 is a schematic depiction of an apparatus comprising multiple devices according to an embodiment of the present invention.

FIG. 4 depicts an embodiment of an apparatus 220, which comprises housing 240. Multiple detection devices 10 are contained within housing 240, which comprises inlet 260 and outlet 280. As mentioned earlier, detection devices 10 may comprise the same or different electrogenic bacterium 14 depending on the nature of use of the apparatus 220.

DEFINITIONS

The following provides definitions for terms and phrases used above, which were not previously defined.

The phrase "at least" as used herein means that the number of specified items may be equal to or greater than the number recited. The phrase "about" as used herein means that the number recited may differ by plus or minus 10%; for example, "about 5" means a range of 4.5 to 5.5. The term "between" when used in conjunction with two numbers such as, for example, "between about 2 and about 50" includes both of the numbers recited as well as fractions of the numbers 2 to 50. As used herein, the singular forms "a", "an" and "the" include plural referents unless the content clearly dictates otherwise. In some embodiments, "a" or "an" as used herein means "at least one" or "one or more." The designations "first" and "second" are used solely for the purpose of differentiating between two items such as "first electrode" and "second electrode" and are not meant to imply any sequence or order or importance to one item over another or any order of operation, for example.

EXAMPLES

The following example describes the preparation and use of a device for monitoring VOC emissions in an industrial plant. An electrogenic bacterium known to metabolize hydrocarbons is selected, namely, *Geobacter metallireducens*, which may be obtained from hydrocarbon-contaminated aquatic/ground water sediments. The sediment is mixed with an equal quantity of nutrient media and incubated under strict anaerobic conditions. The bacteria are incubated at room temperature and in the dark and used or propagated within 14 days. Electricity production from this sample is verified by inoculating the bacteria into a microbial fuel cell configuration with a hydrocarbon analyte suspected of being in the VOC emission as a fuel source.

A device such as depicted in FIGS. 1 and 3 is prepared. Electrode 12 is prepared by propagating the *Geobacter metallireducens* bacterium 14 on the surface of an electrically conductive carbon foam electrode to form a coating of the bacterium at a thickness of about 40 microns. Electrode 16 is an electronically conductive graphite cloth electrode and is separated from electrode 12 by means of separator 18, which is formed from NAFION® electrically insulating material. Electronic circuit 20 electrically connects electrode 12 and electrode 16 and comprises an antenna and a quartz crystal oscillator for generating an RF signal for remote detection. Detection device 10 is contained in housing 24, which is an environmental chamber permeable to the analyte of interest. The contained device forms apparatus 22. Housing 24 comprises inlet 26 and outlet 28 for admitting ambient air suspected of containing VOCs into housing 24. Apparatus 22 is placed in an industrial plant, in which volatile organic compounds (VOC) are employed, to continuously monitor VOC emission. RF signal produced is remotely detected to monitor excess VOC emissions.

The above example is repeated using gold mesh in place of carbon foam for electrode 12 and platinum mesh in place of graphite cloth for electrode 16.

The following example describes the preparation of a device for the detection of explosive materials. A device such as depicted in FIGS. 1 and 3 is prepared. In the following example the device may be affixed to any surface such as, for example, a robotic surface. An electrogenic bacterium 14 *Enterobacter cloacae*, which is adaptively evolved to TNT, is propagated on electrode 12, which is a gold mesh electrode such that a biofilm of approximately 40 microns is formed. Adaptive evolution of *Enterobacter cloacae* is achieved through serial exposure of the bacterium to TNT. The amount of TNT in the propagating media is gradually increased until the bacterium is being propagated solely on TNT. This is achieved by transferring an aliquot of the bacteria in the existing media into media containing a larger fraction of TNT. The original propagating fuel in this example is glucose. The electricity production of the bacteria on the electrode is confirmed by connecting electrode 12 to electrode 16, which is an electronically conductive gold mesh electrode and which is separated from electrode 12 by means of separator 18, which is made of NAFION® membrane, an electrically insulating material capable of conducting protons (and other positively charged ions). Electrode 12 is exposed to a material thought to comprise TNT and the current flowing from electrode 12 to electrode 16 is monitored using a voltmeter. Electrodes 12 and 16 and separator 18 can be configured in any manner and on any substrate that allows for electrons to flow between electrodes 12 and 16 and for separator 18 to separate the electrodes electrically. In this example the electrodes are placed in a TEFLON® polymeric substrate. The electronic circuit 20 is also placed in the substrate and connects electrodes 12 and 16 and contains electrochromic device to induce a color change in response to current flowing between electrodes 12 and 16 in response to the presence of TNT. In this example multiple detection devices 10 are formed and placed on the same substrate and are all contained in housing 24, which is an environmental chamber, which is permeable to TNT and designed to protect devices 10 from contaminants such as, for example, one or more of dust, water and wind. The contained device forms apparatus 220. Housing 24 comprises inlet 260 and outlet 280 for admitting ambient air suspected of containing TNT and for purging the system. Apparatus 220 is placed on a robot or any surface where TNT is expected to continuously monitor the environment for TNT. A colorimetric signal produced as a result of the presence of TNT is remotely detected.

The above example is repeated wherein *Desulfovibrio* sp, which is adaptively evolved to TNT, is employed in place of *Enterobacter cloacae* as a coating on the electrode 12.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A device for detecting a substance in a medium, the device comprising an electrogenic bacterium that is genetically modified by genetic engineering or adaptive evolution to selectively interact with the substance to produce electrons wherein a portion of the electrons provides power to the device and wherein a portion of the electrons generates a signal as an indication of the presence of the substance in the medium, wherein the substance is an analyte or is produced as a result of the presence of the analyte in the medium, the substance being reactive with a substance precursor, the analyte acting to cleave the substance precursor to release the substance.

2. The device for detecting a substance in a medium of claim 1, the device further comprising:
   (a) a first electrode comprising the electrogenic bacterium;
   (b) a second electrode that is an electron acceptor of the portion of the electrons to provide power to the device received from the first electrode; and
   (c) a signal generator that receives from the first electrode the portion of the electrons to generate the signal,
   wherein the device is confined in a housing that provides an environmental barrier.

3. The device according to claim 2, wherein the signal generator comprises an electronic circuit to transfer electrons from the first electrode to the second electrode to generate the signal and to power the device.

4. The device according to claim 2, further comprising a separator disposed between the first electrode and the second electrode, the separator being a proton conducting membrane.

5. The device according to claim 2, wherein first electrode comprises a substrate and the electrogenic bacterium is a coating on a surface of the substrate.

6. The device according to claim 1, wherein the electrogenic bacterium is from the family *Geobacter* or the family *Shewanella* or the family *Enterobacter* or the family *Desulfovibrio*.

7. The device according to claim 1, wherein the electrogenic bacterium is selectively reactive with the substance selected from the group consisting of volatile organic compounds, semi-volatile organic compounds, proteins, polysaccharides, medications, drugs of abuse, pollutants, toxins, forensic substances, explosive residues and acid vapors.

8. A device for detecting an analyte in a medium, the device comprising:
   (a) a first electrode comprising an electrogenic bacterium wherein the electrogenic bacterium is genetically modified to be selectively reactive with a substance to generate electrons and wherein the substance is the analyte or is produced as a result of the presence of the analyte in the medium, the substance being reactive with a substance precursor, the analyte acting to cleave the substance precursor to release the substance;
   (b) a second electrode that is an electron acceptor of electrons produced at the first electrode wherein electrons are received from the first electrode to provide power to the device; and
   (c) a signal generator that produces a signal from the electrons.

9. The device according to claim 8 confined in a housing that provides an environmental barrier.

10. An apparatus comprising a housing and one or more devices according to claim 8.

11. The device according to claim 8 wherein the electrogenic bacterium is from the family *Geobacter* or the family *Shewanella* or the family *Enterobacter* or the family *Desulfovibrio*.

12. The device according to claim 8 wherein the electrogenic bacterium is selectively reactive with the substance selected from the group consisting of volatile organic compounds, semi-volatile organic compounds, proteins, polysaccharides, medications, drugs of abuse, pollutants, toxins, forensic substances, explosive residues and acid vapors.

13. The device according to claim 8 wherein the signal generator comprises an electronic circuit.

14. The device according to claim 13 wherein the electronic circuit transfers electrons from the first electrode to the second electrode to generate the signal and to power the device.

15. The device according to claim 8 further comprising a separator disposed between the first electrode and the second electrode.

16. The device according to claim 8 wherein the separator is a proton conducting membrane.

17. The device according to claim 8 wherein first electrode comprises a substrate and the electrogenic bacterium is a coating on a surface of the substrate.

18. An apparatus comprising a housing and a plurality of devices to detect an analyte in a medium, a device of the plurality comprising:
  (a) a first electrode comprising an electrogenic bacterium wherein the electrogenic bacterium is genetically modified to be selectively reactive with a substance to generate electrons and wherein the substance is the analyte or is produced as a result of the presence of the analyte in the medium, the substance being reactive with a substance precursor, the analyte acting to cleave the substance precursor to release the substance;
  (b) a second electrode that is an electron acceptor of electrons produced at the first electrode wherein electrons are received from the first electrode to provide power to the device;
  (c) an electronic circuit to transfer electrons from the first electrode to the second electrode to generate a signal and to power the device from the electrons, and
  (d) a separator disposed between the first electrode and the second electrode,
  wherein the plurality of devices is confined to the housing, the housing to provide the plurality of devices an environmental barrier.

19. The apparatus according to claim 18 wherein the separator is a proton conducting membrane.

20. The apparatus according to claim 18 wherein the electrogenic bacterium of the device is selectively reactive with the substance selected from the group consisting of volatile organic compounds, semi-volatile organic compounds, proteins, polysaccharides, medications, drugs of abuse, pollutants, toxins, forensic substances, explosive residues and acid vapors.

* * * * *